United States Patent
Roessl et al.

(10) Patent No.: US 10,925,556 B2
(45) Date of Patent: Feb. 23, 2021

(54) IMAGING WITH MODULATED X-RAY RADIATION

(71) Applicant: KONINKLIJKE PHILIPS N.V., Eindhoven (NL)

(72) Inventors: Ewald Roessl, Ellerau (DE); Stewart Young, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 337 days.

(21) Appl. No.: 15/742,645

(22) PCT Filed: Jul. 13, 2016

(86) PCT No.: PCT/EP2016/066596
§ 371 (c)(1),
(2) Date: Jan. 8, 2018

(87) PCT Pub. No.: WO2017/009363
PCT Pub. Date: Jan. 19, 2017

(65) Prior Publication Data
US 2018/0192973 A1 Jul. 12, 2018

(30) Foreign Application Priority Data
Jul. 14, 2015 (EP) .................... 15176597

(51) Int. Cl.
*A61B 6/00* (2006.01)
*G01N 23/04* (2018.01)
*A61B 6/06* (2006.01)

(52) U.S. Cl.
CPC ............. *A61B 6/4014* (2013.01); *A61B 6/06* (2013.01); *A61B 6/40* (2013.01); *A61B 6/4007* (2013.01);
(Continued)

(58) Field of Classification Search
CPC ......... A61B 6/4014; A61B 6/06; A61B 6/544; A61B 6/545; G01N 23/04
See application file for complete search history.

(56) References Cited

U.S. PATENT DOCUMENTS 4,242,588 A 12/1980 Silk
5,077,774 A * 12/1991 Piestrup .............. G03F 7/70033
378/119

(Continued)

FOREIGN PATENT DOCUMENTS

CN 103234987 A 8/2013
EP 2160750 2/2012
(Continued)

OTHER PUBLICATIONS

Schardt, et al., "New x-ray tube performance in computed tomography by introducing the rotating envelope tube technology", Med. Phys. 31 (9), Sep. 2004.
(Continued)

*Primary Examiner* — David P Porta
*Assistant Examiner* — Djura Malevic
(74) *Attorney, Agent, or Firm* — Larry Liberchuk

(57) ABSTRACT

The present invention relates to a modulation of X-ray radiation for the purposes of imaging an object of interest. For the modulation, the X-ray radiation provided by an X-ray source (12) is in part totally reflected by a mirror (20). Thus, an X-ray radiation at an object receiving space (16) is formed by an unreflected X-ray radiation (24) and a reflected X-ray radiation (26). The mirror (20) is displaceable by an actuator (28), such that the intensity of the reflected X-ray radiation (26) can be adjusted, in particular to a density of the object to be imaged.

11 Claims, 8 Drawing Sheets

(52) U.S. Cl.
CPC .............. *A61B 6/542* (2013.01); *A61B 6/544* (2013.01); *A61B 6/545* (2013.01); *G01N 23/04* (2013.01)

(56) References Cited

U.S. PATENT DOCUMENTS

| | | | | |
|---|---|---|---|---|
| 5,206,514 | A * | 4/1993 | Brandner | G21K 4/00 250/484.4 |
| 5,268,951 | A | 12/1993 | Flamholz | |
| 5,757,882 | A * | 5/1998 | Gutman | B82Y 10/00 378/82 |
| 6,863,409 | B2 * | 3/2005 | Cho | H05H 3/06 359/853 |
| 6,917,667 | B2 * | 7/2005 | Fujinawa | G21K 1/06 378/70 |
| 7,039,160 | B2 * | 5/2006 | Hoheisel | A61B 6/06 378/84 |
| 7,330,535 | B2 * | 2/2008 | Arenson | G21K 1/04 378/156 |
| 7,511,902 | B2 * | 3/2009 | Wings | G02B 7/1824 359/822 |
| 7,706,508 | B2 * | 4/2010 | Arenson | G21K 1/04 250/233 |
| 7,966,575 | B1 | 6/2011 | Jetha | |
| 7,978,822 | B2 * | 7/2011 | Windt | A61B 6/4021 378/84 |
| 8,199,883 | B2 * | 6/2012 | Arenson | G21K 1/04 378/156 |
| 8,447,012 | B2 * | 5/2013 | Ichizawa | A61B 6/583 378/113 |
| 8,483,355 | B2 * | 7/2013 | Ichizawa | G01N 23/16 378/53 |
| 8,488,744 | B2 * | 7/2013 | Ichizawa | G01N 23/083 378/156 |
| 8,537,970 | B2 * | 9/2013 | Bernhardt | G21K 1/06 378/84 |
| 8,829,459 | B2 * | 9/2014 | Ichizawa | G01N 23/16 250/375 |
| 2002/0070365 | A1 * | 6/2002 | Karellas | A61B 6/06 250/581 |
| 2004/0264644 | A1 | 12/2004 | Goebel | |
| 2005/0058352 | A1 * | 3/2005 | Deliwala | G01J 3/02 382/232 |
| 2007/0030947 | A1 * | 2/2007 | Popescu | A61B 6/022 378/19 |
| 2007/0104320 | A1 * | 5/2007 | Arenson | G21K 1/04 378/145 |
| 2007/0189444 | A1 * | 8/2007 | Van Steven-Daal | A61B 6/032 378/6 |
| 2009/0041198 | A1 * | 2/2009 | Price | G21K 1/02 378/147 |
| 2009/0147922 | A1 * | 6/2009 | Hopkins | B82Y 10/00 378/140 |
| 2009/0154650 | A1 * | 6/2009 | Tanabe | A61N 5/1042 378/137 |
| 2009/0190720 | A1 * | 7/2009 | Windt | A61B 6/4021 378/146 |
| 2011/0122993 | A1 * | 5/2011 | Ichizawa | G01N 23/083 378/51 |
| 2011/0147603 | A1 * | 6/2011 | Ichizawa | G01N 23/16 250/375 |
| 2011/0299658 | A1 | 12/2011 | Bernhardt | |
| 2012/0051499 | A1 * | 3/2012 | Lee | A61B 6/032 378/16 |
| 2012/0269321 | A1 * | 10/2012 | Behling | H01J 35/24 378/62 |
| 2013/0114795 | A1 * | 5/2013 | Komoto | G21K 1/00 378/145 |
| 2014/0044239 | A1 | 2/2014 | Gendreau | |

FOREIGN PATENT DOCUMENTS

| | | |
|---|---|---|
| JP | 07239310 A | 9/1995 |
| JP | 2011112561 | 6/2011 |
| JP | 2011164043 A * | 8/2011 |
| WO | 2010/051469 | 5/2010 |

OTHER PUBLICATIONS

Hahn, et al., "Grid-controlled fluoroscopy in paediatric radiology", Medicamund, vol. 41, Issue 1, Mar. 1997.

* cited by examiner

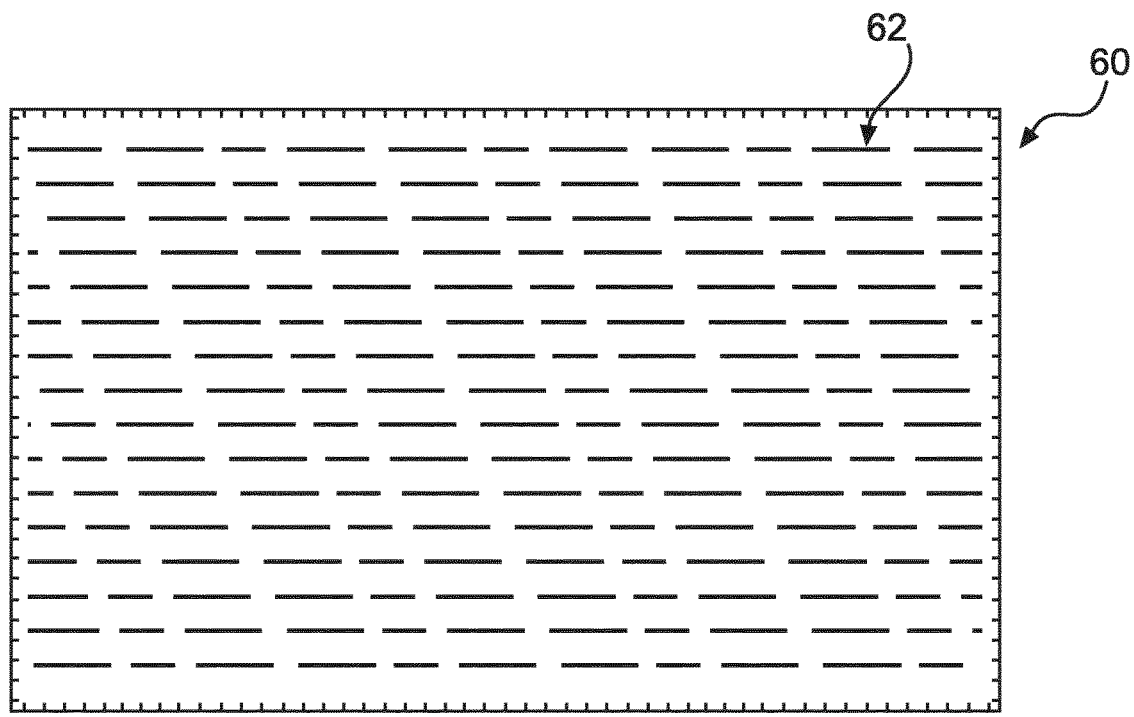
Fig.8
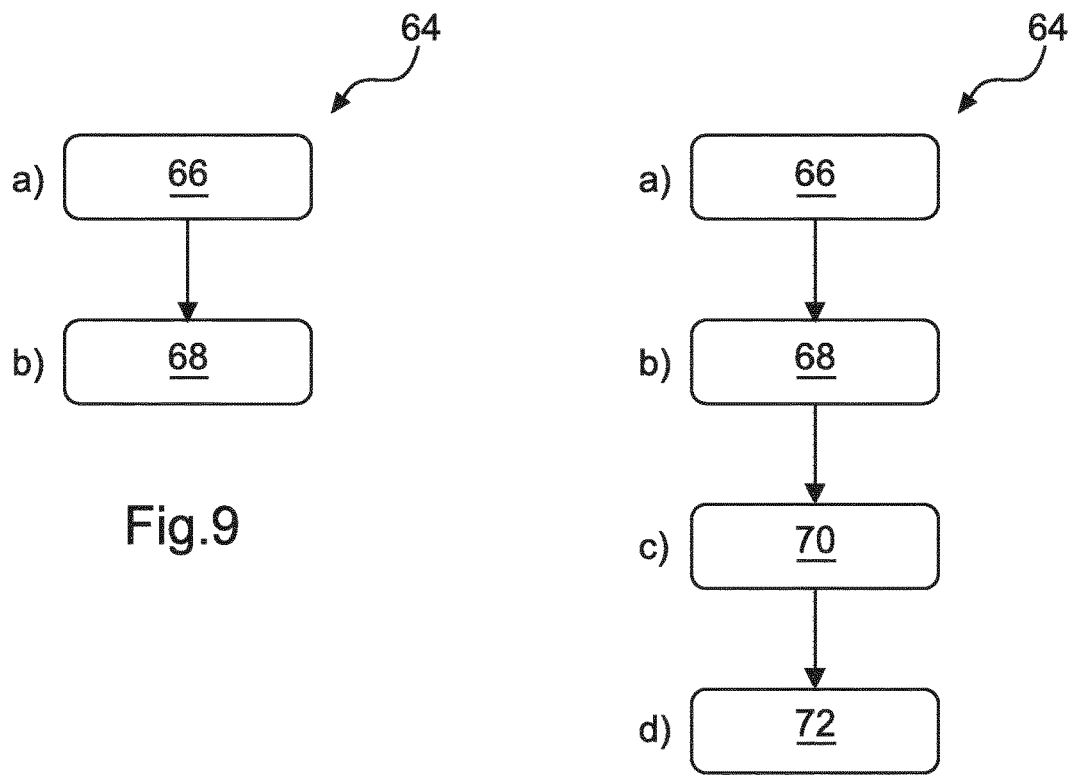
Fig.9
Fig.10

IMAGING WITH MODULATED X-RAY RADIATION

CROSS REFERENCE TO RELATED APPLICATIONS

This application is the U.S. National Phase application under 35 U.S.C. § 371 of International Application No. PCT/EP2016/066596, filed Jul. 13, 2016, published as WO 2017/009363 on Jan. 19, 2017, which claims the benefit of European Patent Application Number 15176597.1 filed on Jul. 14, 2015. These applications are hereby incorporated by reference herein.

FIELD OF THE INVENTION

The present invention relates to an imaging of an object of interest with modulated X-ray radiation, and relates in particular to an X-ray imaging apparatus, an X-ray imaging system and an X-ray imaging method for a modulation of an X-ray radiation.

BACKGROUND OF THE INVENTION

X-ray radiation can be employed for imaging an object of interest. One exemplary application for the use of X-ray radiation is in medical imaging applications, for instance in a computer tomography system or CT system. An X-ray radiation source, for example an X-ray tube, generates X-ray radiation. A detector for detecting X-ray radiation is usually located at a distance from the X-ray radiation source. An object of interest can be arranged between the X-ray radiation source and the detector. The detector converts X-ray radiation, especially X-ray radiation attenuated by the object of interest, to electrical signals, especially for a subsequent reconstruction and for displaying of an image of the object of interest.

The X-ray radiation source and the X-ray radiation detector can be moved in parallel relatively to the object of interest, in order to scan the object of interest with respect to the direction of the movement. With respect to the thickness of the object of interest or with respect to its density, the speed of the movement can be adjusted, such that the statistics of the image acquisition allows obtaining images with low noise over the entire field-of-view (FOV). According to an alternative approach, the intensity of the X-ray radiation provided by the X-ray radiation source is adapted with respect to the thickness or the density of the object of interest.

Document US 2012/0269321 A1 relates to an X-ray radiation source. A X-ray beam can be deflected within the X-ray radiation source, in order to enable a change in the intensity of the X-ray radiation provided. As a result of reflecting the X-ray radiation within the X-ray radiation source, a change in the intensity of the X-ray radiation refers to the whole X-ray radiation provided by the X-ray radiation source. Furthermore, a retrospectively adaptation of an existing X-ray radiation source with elements for internal reflection would need a high effort to provide an X-ray radiation source as explained previously.

Document JP2011112561 A relates to an X-ray measurement system where a specimen is irradiated with direct X-rays and/or X-rays reflected via an X-ray mirror.

SUMMARY OF THE INVENTION

Thus, there is a need to provide an X-ray radiation apparatus, an X-ray radiation system and an X-ray radiation method for providing an X-ray radiation at an object-receiving space, wherein the intensity of the X-ray radiation can be easily adjusted to a desired level.

The object of the present invention is solved by the subject-matter of the independent claims, wherein further embodiments are incorporated in the dependent claims.

It should be noted that the following described aspects of the invention apply for the X-ray imaging apparatus, for the X-ray imaging system and also for the method for a modulation of an X-ray radiation.

According to a first aspect of the present invention, an X-ray imaging apparatus is provided. The X-ray imaging apparatus comprising a source for generating X-ray radiation, a detector for detecting X-ray radiation, an object-receiving space for arranging an object of interest for X-ray imaging and an X-ray radiation modulation arrangement. The object-receiving space is arranged between the source and the detector. The X-ray radiation modulation arrangement is arranged between the source and the object-receiving space. The X-ray radiation modulation arrangement comprises at least one mirror for modulating X-ray radiation by providing a total reflection of a part of the X-ray radiation of the source at the at least one mirror in order to deflect the part of the X-ray radiation towards the detector, such that in the region of the object-receiving space X-ray radiation is provided in form of unreflected primary X-ray radiation in combination with secondary X-ray radiation by the total reflection. The modulation arrangement further comprises at least one actuator to displace the at least one mirror at least between a first position and a second position. A ratio of an intensity of the secondary X-ray radiation to the intensity of the primary X-ray radiation is higher at the first position of the at least one mirror than at the second position of the at least one mirror. There is further provided: a collimation arrangement between the source and the detector. The collimation arrangement comprises a pre-collimator that comprises a plurality of pre-collimator apertures for providing a plurality of X-ray beams to the object receiving space. The pre-collimator is arranged between the modulation arrangement and the object receiving space; and wherein the modulation arrangement comprises for each pre-collimator aperture at least one associated mirror of the at least one mirror.

As a result, the intensity of the X-ray radiation at the object receiving space depends on the intensity of the secondary X-ray radiation. The intensity of the X-ray radiation can be adjusted to a desired level by controlling a displacement of the at least one mirror. By displacing the at least one mirror, an angle of incidence of the part of the X-ray radiation striking a surface of the at least one mirror changes. In case the angle of incidence increases, the total reflection and thus the intensity of the secondary radiation may decrease. The at least one mirror is displaceable by the at least one actuator. Thus, by controlling the actuator an adjustment of the intensity of the X-ray radiation at the object receiving space can be provided without a high effort.

The term "X-ray imaging apparatus" can also be referred to as "imaging apparatus".

The term "source" can also be referred to as "X-ray source".

The term "detector" can also be referred to as "X-ray detector".

The term "X-ray radiation modulation arrangement" is also referred to as "X-ray modulation arrangement", "modulation arrangement" or "modulator".

The term "at least one mirror" can also be referred to as "at least one X-ray mirror".

The term "intensity" relates to the power transferred per unit area perpendicular to the propagation direction of the x-rays. In particular, an average power transferred over one time period of an X-ray radiation may be understood as the intensity of the X-ray radiation.

The at least one mirror can be configured to totally reflect X-ray radiation.

In an example, the X-ray radiation source is employed for generating X-ray radiation used for medical imaging applications, inspection imaging applications or security imaging applications.

In an example, the X-ray radiation source comprises an electron emitting element, e.g. a cathode element, and an electron collecting element, e.g. an anode element. Electrons can be accelerated from the electron emitting element to the electron collecting element by a potential between the two elements for generating X-ray radiation. The electrons emanating from the electron emitting elements may travel to the electron collecting element and can arrive at an area called the focal spot, so creating electro-magnetic radiation.

The object-receiving space relates to a space designated for arranging an object of interest. The object-receiving space may comprise an object support arrangement, for example a pair of pads to hold and (temporarily) fix an object of interest, in particular a breast of a woman, for X-ray examination purposes.

In an example, the detector is configured to detect X-ray radiation, in particular X-ray radiation provided by the source. The detector can be configured to provide a signal, which preferably corresponds to the intensity of the X-ray radiation detected.

As a result, the X-ray imaging apparatus can provide a signal, namely the signal provided by the detector, for imaging purposes. In particular, the signal can be used to reconstruct an image of an object being arranged at the object receiving space.

The X-ray radiation modulation arrangement relates to an arrangement for modulating X-ray radiation.

In an example, the modulation refers to the intensity of the X-ray radiation. In an example, the term "total reflection" refers to a reflection of an X-ray radiation wave, which strikes a boundary of a medium at an angle smaller than a particular critical angle $\theta_c$ with respect to plane level of the boundary. The critical angle $\theta_c$ is the angle of incidence below which the total reflection occurs. In an example, the critical angle $\theta_c$ is defined as: $\theta_c = 1.6 \cdot 10^{-3} \cdot \rho^{0.5} \cdot \lambda$, where $\rho [g/cm^3]$ relates to the density of the medium and $\kappa [\text{Å}]$ relates to the wavelength of the X-ray radiation wave.

The term "unreflected primary X-ray radiation" relates to X-ray radiation generated by the source, wherein this X-ray radiation reaches the object-receiving space without being reflected.

The term "secondary X-ray radiation" relates to the part of the X-ray radiation generated by the source, which has been totally reflected at the at least one mirror of the modulation arrangement and reaches the object receiving space.

In an example, a combination of the primary X-ray radiation and the secondary X-ray radiation relates to a superposition of the primary X-ray radiation and the secondary X-ray radiation. Interference between the primary X-ray radiation and the secondary X-ray radiation may occur.

As a result, the intensity of the X-ray radiation at the object receiving space depends on both, the primary X-ray radiation and the secondary X-ray radiation. Accordingly, the intensity of the X-ray radiation at the object receiving space can be adjusted at least in part by adjusting the intensity of the secondary X-ray radiation. As a result, the intensity of the secondary X-ray radiation can be controlled with the at least one actuator. Thus, the X-ray radiation apparatus provides a flexibility in adjusting the X-ray intensity.

In a further example, the at least one actuator is a linear actuator, in particular an electronic linear actuator. For instance, the at least one actuator can be realized in the form of a motorized stage or a piezo-electric actuator or a microsystem structure actuator.

In an example, the at least one mirror is configured for a continuous displacement between its first position and its second position.

As a result, the intensity of the secondary X-ray radiation may change continuously with a displacement of the at least one mirror from a maximum intensity to a minimum intensity, or vice versa. The minimum intensity can be zero.

In an example, the at least one mirror is displaceable between three, four, five, six, seven, eight, or more positions, in particular between the first position of the at least one mirror and the second position of the at least one mirror.

As a result, the intensity of the secondary X-ray radiation may change stepwise in accordance the respective position from a maximum intensity to a minimum intensity, or vice versa. The minimum intensity can be zero.

In an example, a mechanical bearing for the at least one mirror is provided. The bearing can be configured for constraining the displacement of the at least one mirror along a trajectory between the first position and the second position.

According to an exemplary embodiment, a control unit is provided for determining an attenuation of the intensity of the X-ray radiation in form of a combination of the primary X-ray radiation and of the secondary X-ray radiation at the object-receiving space and for controlling the modulation arrangement depending on the attenuation.

The term "attenuation" relates to a gradual loss in intensity of an X-ray radiation flux, in particular through the absorption of x-rays in the region of the object-receiving space within an object of interest.

As a result, the intensity can be controlled to a desired level, in particular to a level, which corresponds to a desired dose of X-ray radiation to be applied to a particular portion of an object of interest.

In an example, the control unit receives from the source a signal representing the X-ray radiation generated by the source. For the case that no object is arranged in the object-receiving space, the control unit can be configured for determining a primary reference intensity of the intensity of the primary X-ray radiation. In an example, the control unit can (also) be configured for determining a secondary reference intensity of the secondary X-ray radiation in case no object is arranged in the object-receiving space.

In an example, the detector is configured to detect the primary X-ray radiation and/or the secondary X-ray radiation, especially in case an object of interest is arranged at the object receiving space.

In an example, a detector signal representing the detected primary X-ray radiation and/or the detected secondary X-ray radiation is provided to the control unit.

In an example, a signal representing the X-ray radiation provided by the source is provided to the control unit.

In an example, the control unit can be configured to control the at least one actuator, the displacement of the at least one mirror and/or the intensity of the secondary X-ray radiation on the basis of the primary reference intensity, the secondary reference intensity, the detected primary X-ray radiation, the detected secondary X-ray radiation and/or the intensity of the X-ray radiation provide by the source.

The term "controlling the modulation arrangement" relates to controlling the displacement of the at least one mirror and/or controlling the at least one actuator.

According to the invention, a pre-collimator is provided that comprises a plurality of pre-collimator apertures for providing a plurality of X-ray beams to the object receiving space. The pre-collimator is arranged between the modulation arrangement and the object receiving space. The modulation arrangement comprises for each pre-collimator aperture at least one associated mirror of the at least one mirror.

As a result, collimated X-ray radiation is provided to the object receiving space. By collimating the X-ray radiation, an unnecessary X-ray dose to the object of interest can be reduced by the suppression of the detected fraction of scattered radiation.

The pre-collimator relates to an optical arrangement.

In a further example, each aperture of the pre-collimator is formed as a slit. In an example, the pre-collimator is configured for providing collimated X-ray radiation beams to the object-receiving space.

In an example, each aperture of the pre-collimator is configured to collimate X-ray radiation.

In an example, a primary part of the X-ray radiation provided by the source is directed to the pre-collimator, such that in the region of the object-receiving space, primary X-ray radiation is unreflected provided in the form of collimated X-ray beams.

In a further example, the mirrors are configured for guiding a secondary part of the X-ray radiation provided by the source in order to deflect the secondary part of the X-ray radiation towards the pre-collimator, such that in the region of the object-receiving space, secondary X-ray radiation is provided in form of collimated X-ray beams.

According to a further example, a post-collimator is provided, that comprises for each aperture of the pre-collimator an associated post-collimator aperture. Further preferably, a detector arrangement is provided, that comprises a plurality of detectors. The post-collimator is arranged between the object-receiving space and the detector arrangement. Further, for each aperture of the post-collimator one of the detectors is associated and arranged for detecting X-ray radiation passing the respective aperture of the post-collimator, such that an aperture-dependent detector signal is provided. Further preferably, a controller is provided to control, based on the aperture-dependent detector signal, an individual displacement of the mirrors or a displacement in groups of at least two mirrors.

The post-collimator relates to an optical element. The post-collimator apertures of the post-collimator are apertures in the sense of optical elements.

In an example, the post-collimator apertures are configured to provide collimated X-ray radiation to the detector.

According to an example, each post-collimator aperture is formed as a slit. According to an aspect of the invention, an imaging apparatus is provided. The imaging apparatus is configured to adjust the intensity of the X-ray radiation at an object receiving space to a desired level. The adjustment can be performed by modulating the intensity of a secondary X-ray radiation.

A higher intensity of the X-ray radiation at the object-receiving space allows to improve the image quality of an object, that has a large thickness or a high density. However, the high intensity of the X-ray radiation at the object-receiving space is not always needed. In case the object of interest has a low thickness or a low density, a lower intensity of the X-ray radiation at the object receiving space can be suitable for providing a sufficient image quality of the object. Accordingly, a high intensity of the X-ray radiation at the object-receiving space would increase the X-ray radiation dose to the object of interest without significantly improving the image quality.

Furthermore, an object of interest may not have a uniform density or a uniform thickness with respect to its lateral extension. Providing a high uniform X-ray radiation to such an object of interest may be suitable for an area of the object of interest, where the respective density or thickness is high. However, the high uniform X-ray radiation may provide a too high intensity of X-ray radiation to another area of the object of interest, where the density or the thickness of the object of interest is low. Therefore, the X-ray imaging apparatus is suggested, that provides an X-ray radiation modulation arrangement. The X-ray radiation arrangement is provided between the source for generating the X-ray radiation and the object-receiving space. A pre-collimator is further provided, which is arranged between the modulation arrangement and the object-receiving space. The pre-collimator comprises a plurality of apertures. The apertures are configured to form collimated X-ray beams, in case X-ray radiation is attenuated at the pre-collimator. The X-ray radiation provided by the source may be categorized in several parts. One part of the X-ray radiation shall relate to the so-called primary part of the X-ray radiation, which is directed to the object-receiving space without being reflected by the modulation arrangement or the pre-collimator arrangement. Consequently, the primary part of the X-ray radiation provided by the source forms the primary X-ray radiation at the object-receiving space. A so-called second part of the X-ray radiation provided by the source is directed to the modulation arrangement. The modulation arrangement provides a plurality of mirrors and a plurality of actuators. For each aperture of the pre-collimator, an associated set of mirrors of the modulation arrangement and an associated actuator of the modulation arrangement can form a group. The apparatus provides a plurality of such groups. Accordingly, the secondary part of the X-ray radiation provided to the modulation arrangement can be reflected at their mirrors to the pre-collimator, where at least a part of the reflected X-ray radiation can pass the apertures of the pre-collimator as secondary X-ray radiation in form of beams. The intensity of each beam can be controlled, as each of the mirrors can be displaced between a first position and a second position by its associated actuator of the respective group. In particular, the secondary part of the X-ray radiation provided by the source can be totally reflected by the mirror of the set of mirrors at their first position. At the second position of the mirrors, the total reflection of the secondary part of the X-ray radiation may not occur or may occur in part, in particular only at a limited part of a surface of the respective mirror. Accordingly, the intensity of the secondary X-ray radiation can be controlled by the displacement of the mirrors. Since the mirrors are associated with an aperture of the pre-collimator and a respective actuator, the intensity of the X-ray beams provided by the apertures of the pre-collimator can be aperture-individually controlled. In other words, the intensity of each X-ray beam of the secondary X-ray radiation can be individually controlled. The individual control of the X-ray beams of the secondary X-ray radiation allows to adjust the secondary X-ray radiation to the density or the thickness of the object of interest, in particular at the position of the object of interest, where the X-ray beams of the secondary X-ray radiation are applied to. Furthermore, a post-collimator arrangement and a detector arrangement are provided for the apparatus. The post-collimator arrangement provides for each aperture of the pre-collimator an associated aperture. The object-receiving space is arranged between the pre-collimator and the post-collimator. Accordingly, the X-ray radiation passing the pre-collimator is, at least partly, directed to the associated apertures of the post-collimator. The detector arrangement is arranged behind the post-collimator, such that the post-collimator is arranged between the object-receiving space and the detector arrangement. The detector arrangement comprises for each aperture of the post-collimator an associated detector. Each detector is furthermore aligned with the associated aperture of the post-collimator, such that the detector can detect X-ray radiation passing the associated aperture of the post-collimator. When controlling the displacement of a mirror in order to modulate the X-ray beam passing the associated aperture of the pre-collimator, the detector may detect an intensity of X-ray radiation, which corresponds to an attenuated intensity of the primary X-ray radiation and the secondary X-ray radiation. The controller may be supplied with a signal corresponding to the intensity of the X-ray radiation provided by the source. Accordingly, the controller can control the displacement of the mirrors based on an attenuation of the intensity of the primary X-ray radiation and/or the attenuation of the secondary X-ray radiation. Since the detectors of the detector arrangement are each associated with an aperture of the post-collimator, an aperture of the pre-collimator and a set of mirrors, the control of the displacement of the mirrors can be performed for each set of mirrors individually with respect to the signal of the respective detector. Further, the X-ray radiation provided to the object-receiving space can be controlled individually for each aperture of the pre-collimator. Therefore, the intensity of the X-ray radiation applied to an object of interest can be controlled position-dependent and thus being adjusted to the local density or thickness of the object of interest. This adjustment increases the image quality as well as reduces the dose applied to the object of interest to a suitable minimum.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 8 shows a schematic setup of a slit arrangement;

FIG. 9 shows a flowchart of a first example of the method; and

FIG. 10 shows a flowchart of a second example of the method.

DETAILED DESCRIPTION OF EMBODIMENTS

Figure 1:
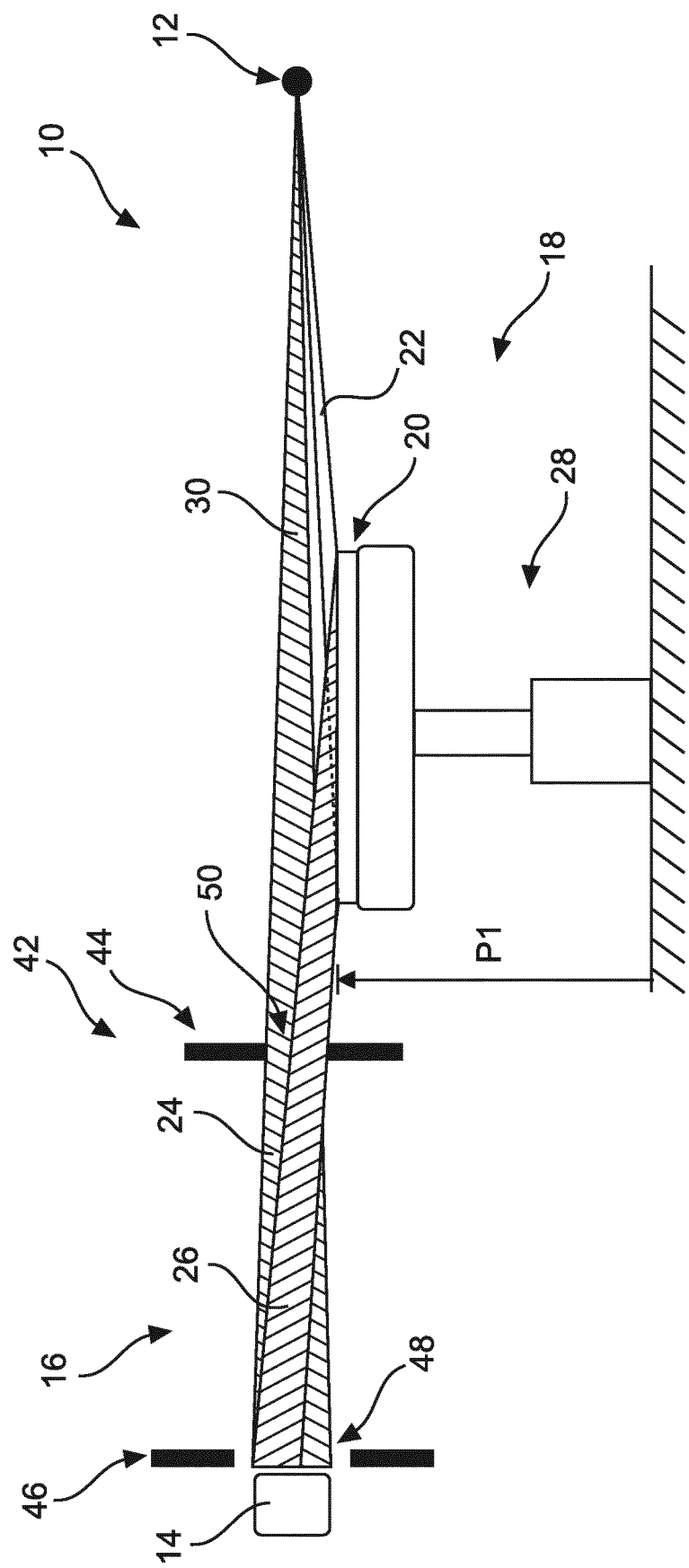
FIG. 1 shows a schematic setup of a first example of the X-ray imaging apparatus.

FIG. 1 shows an example of the X-ray imaging apparatus 10 in a schematic setup. The X-ray imaging apparatus 10 comprises a source 12, a detector 14, an object-receiving space 16 and an X-ray radiation modulation arrangement 18. The source 12 is configured for generating X-ray radiation.

The detector 14 is configured for detecting X-ray radiation.

The object-receiving space 16 is configured for arranging an object of interest (not shown) for X-ray imaging.

The X-ray radiation modulation arrangement 18 is configured for modulating X-ray radiation, in particular with respect to its intensity.

The X-ray radiation modulation arrangement 18 also relates to as "X-ray modulation arrangement", "modulation arrangement" or "modulator".

The object-receiving space 16 is arranged between the source 12 and the detector 14.

The X-ray radiation modulation arrangement 18 is arranged between the source 12 and the object-receiving space 16.

The X-ray radiation modulation arrangement 18 comprises at least one mirror 20 for modulating X-ray radiation by providing a total reflection of a part 22 of the X-ray radiation of the source 12 at the at least one mirror 20 in order to deflect the part 22 of the X-ray radiation towards the detector 14, such that in the region of the object-receiving space 16, X-ray radiation is provided in form of unreflected primary X-ray radiation 24 in combination with secondary X-ray radiation 26 by the total reflection.

The X-ray radiation modulation arrangement 18 further comprises at least one actuator 28 to displace the at least one mirror 20 at least between a first position P1 and a second position P2.

A ratio of an intensity of the secondary X-ray radiation 26 and an intensity of the primary X-ray radiation 24 is higher at the first position P1 of the at least one mirror 20 than at the second position P2 of the at least one mirror 20.

As a result, the X-ray radiation provided to the object-receiving space 16 can be modulated in its intensity. The intensity of the secondary X-ray radiation 26 is therefore adjustable by the displacement of the at least one mirror 20.

In case a higher intensity of the X-ray radiation at the object-receiving space 16 is needed, the at least one mirror 20 may be displaced to its respective first position P1, such that a higher intensity of the combination of the primary X-ray radiation 24 and the secondary X-ray radiation 26 is provided to the object-receiving space 16.

In case lower intensity of X-ray radiation at the object-receiving space 16 is needed, the at least one mirror 20 can be displaced to its respective second position P2, such that the intensity of the X-ray radiation at the object-receiving space 16 is decreased. At the second position P2 of at least one mirror 20 an angle of incidence of an X-ray radiation provided by the source 12 may be, at least in part, be larger than a critical angle. Thus, the X-ray radiation provided by the source 12 and striking a boundary of the at least one mirror 20 may be not or partly not totally reflected. Accordingly, the combination of the primary X-ray radiation 24 and the secondary X-ray radiation 26 has a lower common intensity. Thus, a lower intensity of the X-ray radiation provided to the object-receiving space 16 is provided.

As a result, the intensity of the X-ray radiation provided to the object-receiving space 16 can be adjusted and thus being modulated. By controlling the at least one actuator 28, a displacement of the at least one mirror 20 can be performed. The intensity of the secondary X-ray radiation 26 depends on the position of the at least one mirror 20. Accordingly, by controlling the actuator 28, the intensity of the secondary X-ray radiation 26 at the object-receiving space 16 can be adjusted. Thus, the intensity of the X-ray radiation provided to the object-receiving space 16 can be modulated in its intensity.

In an example, the source 12 is configured for generating X-ray radiation.

In an example, the source 12 for generating X-ray radiation is of the kind, which is generally known in the state of the art.

In a further example, the source 12 is provided by a rigid X-ray source unit, in particular such as an X-ray source of a stationary or rotation kind. Preferably, the source 12 is an X-ray tube or a γ-emitter.

In an example, the X-ray radiation provided by the source 12 has an energy between 10 keV and 40 keV. Preferably, the source 12 comprises a wavelength filter, which is configured for suppressing X-ray radiation having a wavelength corresponding to the energy of less than 10 keV.

In an example, the detector 14 for detecting X-ray radiation is of the kind, which is generally known in the state of the art.

In an example, the detector 14 is configured to provide a detector signal corresponding to an intensity of an X-ray radiation detected. The detector 14 can be configured for providing the detector signal to another unit and/or for further purposes, in particular for imaging purposes.

In an example, the object-receiving space 16 relates to a space designated for arranging an object of interest. The object of interest may be of a biological material.

In an example, the object-receiving space 16 comprises an object support arrangement, for example a pair of pads to hold and temporarily fix a breast for X-ray examination purposes, in particular for screening purposes.

The object-receiving space 16 is arranged between the source 12 and the detector 14.

In an example, the X-ray radiation provided by the source 12 can be categorized or theoretically divided into several parts of X-ray radiation. One of these parts of X-ray radiation can relate to the so-called primary part 30 of the X-ray radiation provided by the source 12.

According to a further example, the X-ray radiation generated by the source 12 comprises at least a primary part 30 and a secondary part 22. Preferably, the primary part 30 has a propagation direction directly towards the detector 14 for forming primary X-ray radiation 24. The secondary part 22 may have a propagation direction directly towards the at least one mirror 20 at its first position P1. Preferably, the at least one mirror 20 is arranged at least in its first position P1 for totally reflecting radiation of the secondary part 22 towards the detector 14 for forming the secondary X-ray radiation 26. Further preferably, for radiating an object of interest, sum of the the primary X-ray radiation 24 and the secondary X-ray radiation 26 provide an effective added X-ray radiation.

As a result, the modulation arrangement 18 is configured such that an enhanced radiation can be provided at the object-receiving space 16.

The X-ray radiation source 12 may comprise further X-ray radiation parts, which may be directed in a direction other than to the detector 14 or to the at least one mirror 20 in its first position P1.

In a further example, the primary part 30 of X-ray radiation is (directly) directed to the object-receiving space 16, in particular without being reflected by the X-ray radiation modulation arrangement 18. When reaching the object-receiving space 16, the primary part 30 of the X-ray radiation forms the primary X-ray radiation 24 at the object-receiving space 16.

In a further example, the secondary part 22 of the X-ray radiation is (preferably directly) directed to the X-ray radiation modulation arrangement 18. In case the secondary part 22 of the X-ray radiation is totally reflected at the at least one mirror 20 of the X-ray radiation modulation arrangement 18 in order to deflect the secondary part 22 of the X-ray radiation towards the detector 14, the reflected secondary part 22 of the X-ray radiation forms a secondary X-ray radiation 26 when reaching the object-receiving space 16.

In an example, only a part of the secondary part 22 of the X-ray radiation is totally reflected at the at least one mirror 20 of the X-ray radiation modulation arrangement 18. This may occur, in case the at least one mirror is at its second position P2 or at another position between the first position P1 and the second position P2.

The at least one mirror 20 preferably relates to a plate with a suitable low atomic number mirror material, in particular with an atomic number lower than nine.

In an example, the at least one mirror 20 relates to a plate of a glass-ceramic.

In a further example, the at least one mirror 20 comprises a lithium aluminosilicate glass-ceramic. A mirror of that kind may have a specific density of 2.53. However, this is just one example for the specific density. Generally, a wide range of possible materials with specific densities for the at least one mirror 20 is possible. Basically, total reflection occurs at the at least one mirror 20 in case the at least one mirror has, with respect to the X-ray radiation, an optically thinner medium at a boundary surface to the space between the source 4 and the at least one mirror 20. Since refractive indices in the X-ray radiation regime are usually smaller than 1, an X-ray total reflection can be observed upon grazing incidents on any material given the incidence occurs within the critical angle of incidence $\theta_c$. The term "critical angle of incidence" can also be referred to as "critical angle". A simplified critical angle of incidence can be calculated as follows: $\theta_c = 1.6 \cdot 10^{-3} \cdot \rho^{0.5} \cdot \lambda$, wherein $\rho$ being the density in the units of g/cm$^3$ and $\lambda$ denotes the X-ray wavelength in Å. The critical angle $\theta_c$ is typically in the order of a few mrad (milli-rad). For example, the critical angle $\theta_c$ may be between 0.5 mrad and 2 mrad. In order to achieve total reflection with larger angles, the density of the material being used for the at least one mirror 20 has to be increased, or metallic coating can be used, for example with silver or gold. In order to achieve total reflection with smaller angles, the density of the material being used for the at least one mirror 20 has to be decreased. For example, the at least one mirror 20 may comprises at least one plastic mirror layer, preferably having low atomic number element. In an example, the term "total reflection" refers to a reflection of an X-ray radiation wave, which strikes a boundary of a medium at an angle $\theta_i$ smaller than a particular critical angle $\theta_c$ with respect to a plane level to the boundary. The critical angle $\theta_c$ is the angle of incidence below which the total reflection occurs.

In an example, the X-ray radiation provided to the object-receiving space 16 relates to a combination of the primary X-ray radiation 24 and the secondary X-ray radiation 26. An interference in the primary X-ray radiation 24 and the secondary X-ray radiation 26 may occur.

In an example, the combination of the primary X-ray radiation 24 and the secondary X-ray radiation 26 leads to a superposition of the primary X-ray radiation 24 and the secondary X-ray radiation 26.

Since the X-ray imaging apparatus 10 is configured for providing a combination of the primary X-ray radiation 24 and the secondary X-ray radiation 26 to the object-receiving space 16, an increase of total flux of X-ray radiation provided to the object-receiving space 16 may occur. Consequently, the X-ray imaging apparatus 10 is a cost-efficient improvement for adjusting the intensity of X-ray radiation being used for imaging an object of interest in the object-receiving space 16. The increase of the total flux of X-ray radiation at the object-receiving space 16 can be useful in case the object-receiving space is provided with an object of interest having a large thickness or a high density. However, in another example, the object-receiving space 16 is provided with an object of interest having a low thickness or a low density. In this case, an increase of the total flux of the X-ray radiation may not be helpful or even increase an X-ray radiation dose to object of interest without increasing an image quality of the object of interest.

In order to adjust the X-ray radiation provided to the object-receiving space 16, the X-ray radiation modulation arrangement 18 is configured for adjusting the intensity of the secondary X-ray radiation 26.

As explained above, the occurrence of total reflection at the at least one mirror 20 depends on the angle of incidence $\theta_i$ of an X-ray radiation wave striking a boundary of the at least one mirror 20. Thus, by controlling the angle of incidence $\theta_i$ of an X-ray radiation wave at the at least one mirror 20, an X-ray radiation flux of the X-ray radiation being reflected at the at least mirror 20 can be controlled.

In an example, the primary part 22 of the X-ray radiation provided by the source 12 is reflected at the at least one mirror 20 towards the detector 14, in case the at least mirror 20 is at its first position P1.

In case the at least one mirror 20 is displaced from its first position P1 to its second position P2, the X-ray radiation flux of the secondary X-ray radiation 26 decreases, since an angle of incidence $\theta_i$ of the secondary part 22 at the at least one mirror 20 increases. Correspondingly, only a part of the secondary part 22 of the X-ray radiation provided by the source 12 is totally reflected at the at least mirror 20 and thus being deflected to the detector 14.

In this case, the angle of incidence $\theta_i$ of the secondary part 22 of the X-ray radiation provided by the source 12 is higher than a critical angle $\theta_c$, the secondary part 22 of the X-ray radiation striking the at least one mirror 20 will not be reflected.

In an example, the angle of incidence $\theta_i$ of the secondary part 22 of the X-ray radiation of the source 12 striking the at least one mirror 20 depends on the position of the at least one mirror. 20. For example, a translational and/or a rotary displacement of the at least one mirror 20 has a influence on the angle of incidence $\theta_i$. Since the at least one actuator 28 of the X-ray radiation modulation arrangement 18 is configured to displace the at least one mirror 20, the intensity of the secondary X-ray radiation 22 is preferably controllable by controlling the at least one actuator 28.

In an example, the displacement of the at least one mirror 20 relates to a translational and/or a rotatory displacement.

In an example, the at least one mirror 20 can be displaced linearly.

In an example, the at least one mirror 20 can be displaced between its first position and its second position along a trajectory.

As a result, a desired behaviour in a change in the intensity of the secondary X-ray radiation 26 can be achieved.

In an example, the X-ray radiation modulation arrangement 18 comprises a mechanical guidance for the at least one mirror 20.

In an example, the at least one actuator 28 can be configured to displace the at least one mirror 20 along a displacement-axis, wherein the displacement-axis and a longitudinal axis between the source 12 and the detector 14 form a angle between 45° and 135°, in particular between 60° and 120°, preferably between 85° and 95°. Accordingly, the at least one mirror 20 can be displaced for example perpendicular to the longitudinal axis.

As a result, a simple structured actuator 28 can be used for the displacement of the at least one mirror 20.

In an example, the at least one mirror 20 is configured for a continuous displacement between the first position P1 of the at least one mirror 20 and the second position P2 of the at least one mirror 20.

As a result, the intensity of the secondary X-ray radiation 26 may change with the displacement continuously from a maximum intensity to a minimum intensity, or vice versa. The minimum intensity can be zero.

In an example, the at least one mirror 20 is displaceable between three, four, five, six, seven, eight, or more positions, in particular between the first position P1 of the at least one mirror 20 and the second position P2 of the at least one mirror 20.

Figure 2:
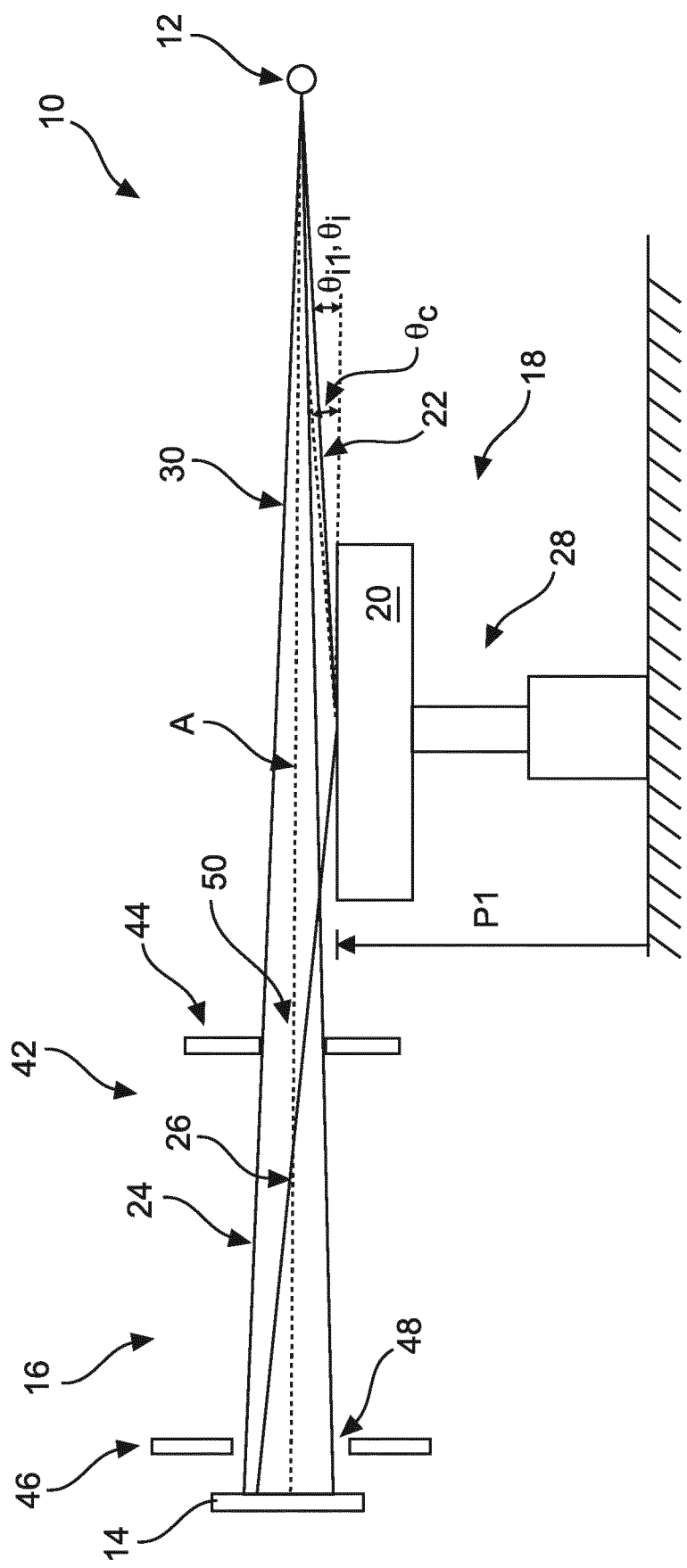
FIG. 2 shows a schematic setup of a second example of the X-ray imaging apparatus, wherein the at least one mirror is in a first position.

FIG. 2 shows a schematic setup of a further example of the X-ray imaging apparatus 10. In principle, this example of the X-ray imaging apparatus 10 corresponds to the previously explained example of the X-ray imaging apparatus 10. Accordingly, reference is made to the explanation with respect to FIG. 1.

In FIG. 2, the secondary part 22 of the X-ray radiation provided by the source 12 is representatively shown in a line directed from the source 12 to the mirror 20. The at least one mirror 20 is at its first position P1. The angle of incidence $\theta i1$ is an angle between the secondary part 22 of the X-ray radiation provided by the source 12 and a plane surface of the at least one mirror 20. The angle of incidence $\theta i1$ is smaller than a critical angle $\theta_c$. Therefore, total reflection occurs on the surface of the at least one mirror 20 with respect to the secondary part 22 of the X-ray radiation provided by the source 12. The reflected X-ray radiation will be deflected to the detector 14 and forming the secondary X-ray radiation 26 in the object-receiving space 16. Consequently, the primary X-ray radiation 24 at the object-receiving space 16 and the secondary X-ray radiation 26 at the object-receiving space 16 are superposing each other, and thus enhancing the X-ray radiation provided to the object-receiving space 16. This enhancement increases the intensity of the X-ray radiation provided to the object-receiving space 16.

Figure 3:
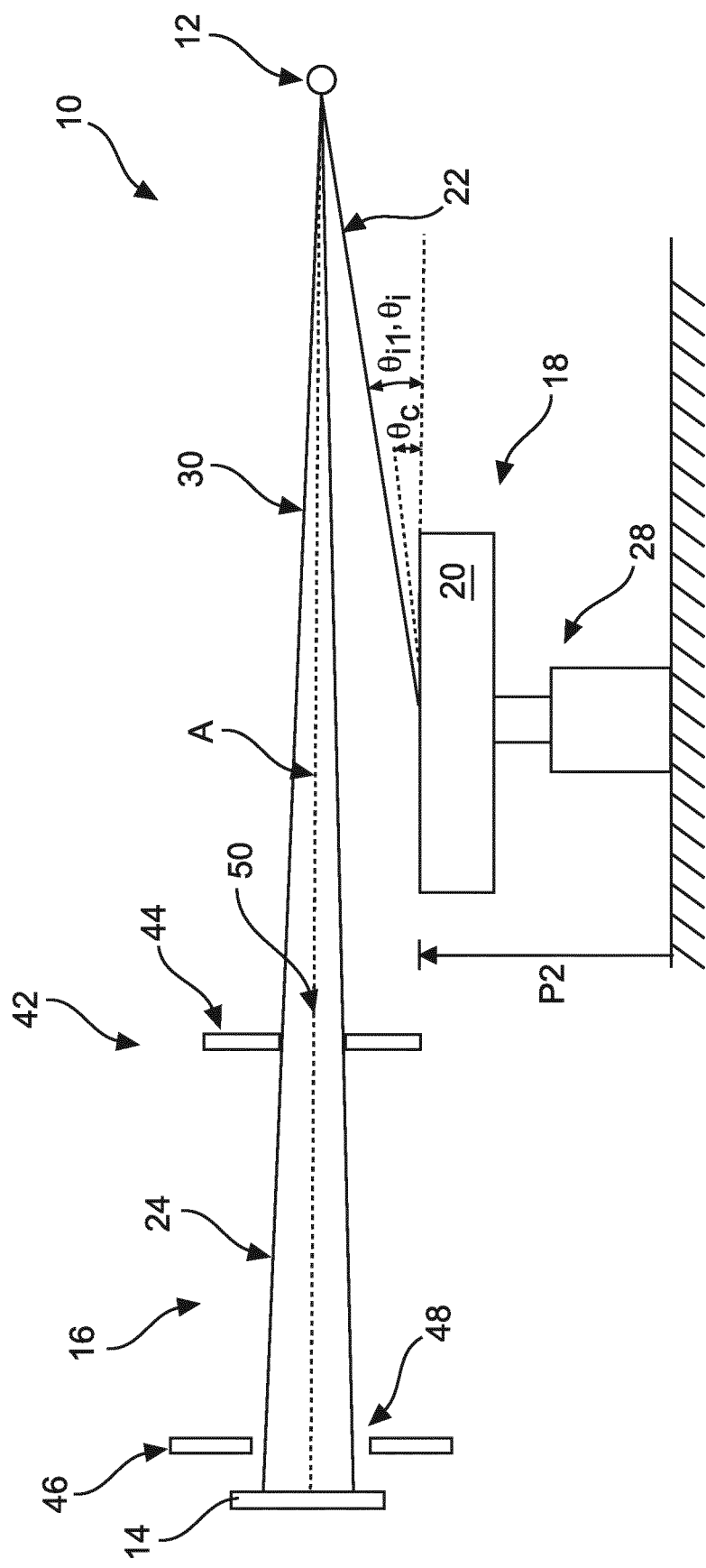
FIG. 3 shows a schematic setup of the second example of the X-ray imaging apparatus, wherein the at least one mirror is in a second position.

FIG. 3 shows an alternative schematic setup of the previously explained example of the X-ray imaging apparatus 10, wherein the at least one mirror 20 is in a second position P2.

The at least one actuator 28 is configured to displace the at least one mirror 20, preferably in a direction perpendicular to the longitudinal axis A between the source 12 and the detector 14. Accordingly, the at least one actuator 28 can displace the at least one mirror 20 linearly between the first position P1 and the second position P2.

The displacement of the at least one mirror 20 changes the angle of incidence θi of the secondary part 22 of the X-ray radiation provided by the source 12 at the at least one mirror 20. The angle of incidence θi has been increased to θi2, such that the angle of incidence θi2 is larger than a critical angle θc. Accordingly, the secondary part 22 of the X-ray radiation provided by the source 12 is not totally reflected when striking upon a surface of the at least one mirror 20.

FIG. 3 exemplarily shows that a displacement of the at least one mirror 20 may result in a decrease of the intensity of the X-ray radiation provided at the object-receiving space 16. The intensity of the X-ray radiation provided to the object-receiving space 16 is formed (in this case) solely by the primary X-ray radiation 24. The secondary part 22 of the X-ray radiation provided by the source 12 is not reflected and cannot contribute in this case to the intensity of the X-ray radiation at the object receiving space 16.

In an example, only a part of the secondary part 22 of the X-ray radiation provided by the source 12 may not be reflected, in case the at least one mirror is at its second position P2. Accordingly, the intensity of the secondary X-ray radiation 26 may not be zero, but less with respect to the case, when the at least one mirror 20 is at its first position P1.

In an example, the modulation of the X-ray radiation at the object-receiving space 16 relates to the intensity of the secondary X-ray radiation 26 at the object-receiving space 16.

Figure 4:
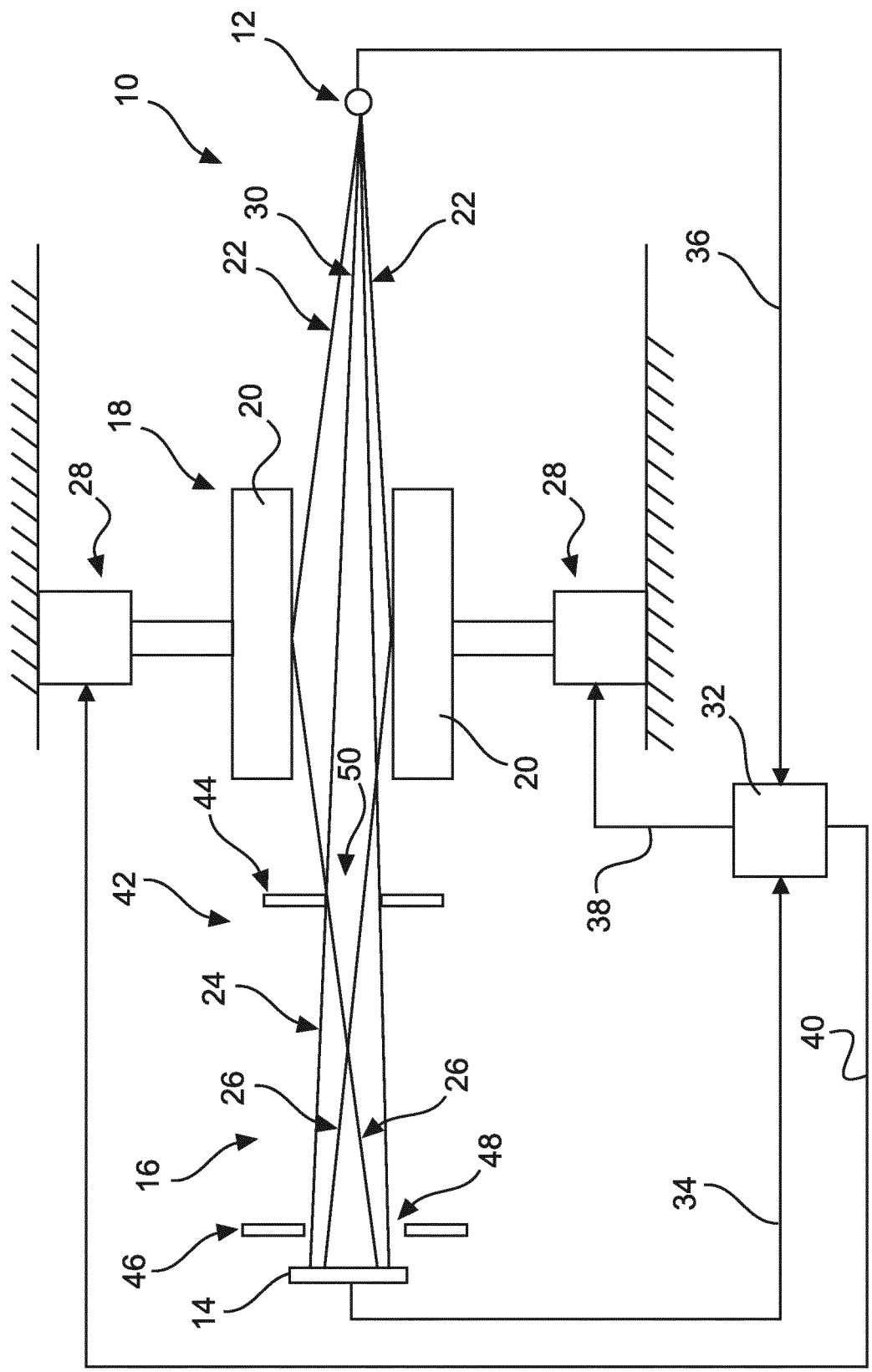
FIG. 4 shows a schematic setup of a third example of the X-ray imaging apparatus.

FIG. 4 shows a schematic setup of a further example of the imaging apparatus 10.

The imaging apparatus 10 is similar to the imaging apparatuses 10 explained with respect to the FIGS. 1 to 3. Thus, reference is made to the previous explanations, where suitable.

In an example, the imaging apparatus 10 comprises a control unit 32 for determining an attenuation of the intensity of the X-ray radiation in form of a combination of the primary X-ray radiation 24 and of the secondary X-ray radiation 26 at the object-receiving space 16 and for controlling the modulation arrangement 18 depending on the attenuation.

As a result, the intensity X-ray radiation provided to the object-receiving space 16 can be adjusted to the density and/or thickness of an object of interest arranged at the object receiving space 16. In case the object of interest provides a high density, a higher attenuation can be expected. In order to maintain a desired image quality of the object of interest, the intensity of the X-ray radiation at the object receiving space 16 can be increased by the control unit 32. The control unit 32 may control a displacement of the at least one mirror 20, such that the secondary X-ray radiation 26 superposes the primary X-ray radiation 24. Thus a higher common intensity is provided.

In an example, the X-ray imaging apparatus 10 is configured, such that control unit 32 receives a signal from the detector 14, whereas the signal is representative for the X-ray radiation detected.

In a further example, a signal line 34 between the detector 14 and the control unit 32 is provided.

In an example, the X-ray imaging apparatus 10 is configured, such that the control unit 32 receives a signal from the source 12 wherein the signal of the source 12 is representative of the X-ray radiation provided to the modulation arrangement 18, especially to its at least one mirror 20, and/or directly to the detector 14.

In a further example, a signal line 36 between the source 12 and the control unit 32 is provided.

In an example, the control unit 32 is configured to receive signals from the detector 14 and the source 12, wherein on the basis of the signals, an attenuation of the X-ray radiation at the object-receiving space 16 can be determined by the control unit 32.

In an example, the control unit 32 is configured to control at least one actuator 28.

In a further example, a signal line 38, 40 between the control unit 32 and the at least one actuator 28 is provided.

In case the control unit 32 received signals, which represent the intensity of the X-ray radiation provided by the source 12 and an intensity of the X-ray radiation impinging the detector 14, the control unit 32 can be configured to determine the attenuation of the X-ray radiation provided to the object receiving space 16.

The X-ray imaging apparatus 10 shown in FIG. 4 comprises two mirrors 20. For each of the mirrors 20 an associated actuator 28 is provided. Each of the actuators 28 is connected via a respective control signal line 38, 40 with the control unit 32. Thus, the control unit 32 can adjust, in particular in accordance with the attenuation of the primary X-ray radiation 24 and/or the attenuation of the secondary X-ray radiation 26, a displacement of the mirrors 20 by controlling the actuators 28.

In an example, the X-ray imaging apparatus 10 comprises a sensor (not shown) configured to detect a spatial parameter of an object of interest. For example, the sensor can be configured for detecting a lateral extension of an object of interest and/or a thickness of an object of interest.

In an example, the control unit 32 is configured for controlling the modulation arrangement 18 depending, in particular also, on the spatial parameter detected by the sensor. For instance, the control unit 32 can control the at least one actuator 28 depending on a lateral extension and/or a thickness of an object of interest, which has been arranged at the object-receiving space 16.

As a result, the control unit 32 can adjust the intensity of the secondary X-ray radiation 26 in accordance with a detected lateral extension, a thickness or any other spatial parameter of an object of interest, which has been arranged at the object-receiving space 16.

FIG. 1 to FIG. 4 show that the at least one mirror 20 is preferably not in conflict with the primary part 30 of the X-ray radiation provided by the source 12.

According to a further example, the at least one mirror 20 is arranged laterally to the primary part 30 of the X-ray radiation provided by the source 12.

As a result, the primary part 30 of the X-ray radiation provided by the source 12 can reach the object-receiving space 16 unhindered, in order to form the primary X-ray radiation 24.

In an example, the at least one mirror 20 is displaceable along a trajectory between its first position P1 and its second position P2. Preferably, the trajectory of the at least one mirror 20 is arranged to intersect a propagation direction of the secondary part 22 of the X-ray radiation provided by the source 12. Further preferably, the trajectory of the at least one mirror 20 is outside a primary part 30 of the X-ray radiation provided by the source 12.

As a result, the at least one mirror 20 can be displaced along its trajectory to a position, where a total reflection of at least a part of the secondary part 22 of the X-ray radiation provided by the source 12 occurs, such that the reflected X-ray radiation forms the secondary X-ray radiation 26 at the object-receiving space 16.

In an example, the trajectory of the at least one mirror 20 and the propagation direction of the secondary part 22 of the X-ray radiation provided by the source 12 form an intersection angle of greater than 0. Preferably, the intersection angle is between 80° and 110°.

According to a further example, the modulation arrangement 18 is configured such that in the first position P1 of the at least one mirror 20, an incidence angle $\theta i1$ of the secondary part 22 of the X-ray radiation provided by the source 12 at the at least one mirror 20 is smaller than a critical angle $\theta c$ of total reflection, and in the second position P2 of the at least one mirror 20, an incidence angle $\theta i2$ of the secondary part 22 of the X-ray radiation provided by the source 12 at the at least one mirror 20 is larger than a critical angle $\theta c$ of total reflection.

As a result, a total reflection of at least a part of the secondary part 22 of the X-ray radiation provided by the source 12 occurs at the first position P1 of the at least one mirror 20. At the second position P2 of the at least one mirror 20, the respective angle of incidence $\theta i2$ is preferably larger than the critical angle $\theta c$, such that a secondary part 22 of the X-ray radiation of the source 12 is not totally reflected, and in particular being absorbed by the at least one mirror 20.

In an example, the at least one mirror 20 comprises a concave reflecting-surface.

In practice, it has been shown that a concave mirror surface may increase the intensity of reflected X-ray radiation.

With respect to FIGS. 1 to 4, the imaging apparatus 10 preferably comprises a collimation arrangement 42.

According to an example, the imaging apparatus 10 comprises a collimation arrangement 42 between the source 12 and the detector 14. The collimation arrangement 42 comprises a pre-collimator 44 arranged between the mirror arrangement 18 and the object-receiving space 16, and a post-collimator 46 arranged between the object-receiving space 16 and the detector 14.

As a result, collimated X-ray radiation is provided to the object-receiving space 16 by the pre-collimator 44.

As a further result, collimated X-ray radiation is provided to the detector 14 by the post-collimator 46.

The pre-collimator 44 relates to an optical element comprising at least one aperture 50. Preferably, each aperture 50 of the pre-collimator 44 is formed as a slit. In an example, the pre-collimator 44 is configured to provide collimated X-ray radiation. In particular, an X-ray radiation can pass the at least one aperture 50 of the pre-collimator 44 as a collimated X-ray beam.

The post-collimator 46 relates to an optical element comprising at least one aperture 48. Preferably, each aperture 48 of the post-collimator 46 can be formed as a slit.

In an example, an X-ray radiation can pass the at least one aperture 48 of the post-collimator 46 as a collimated X-ray beam.

Collimators 44, 46 are generally known in the state of the art. For example, the pre-collimator 44 and/or the post-collimator 46 comprise each a plate, in particular an X-ray absorbing plate, with at least one hole, which may form an aperture 50, 48 of the respective collimator 44, 46.

In an example, an X-ray radiation striking on the plate of the collimator 44, 46 outside the at least one aperture 48, 50 will not pass. Instead, this X-ray radiation will very likely be absorbed by the plate.

In an example, the at least one aperture 50 of the pre-collimator 44 is configured to allow a transmission of the primary part 30 of the X-ray radiation provided by the source 12 and of a secondary part 22 of the X-ray radiation provided by the source 12 and being reflected at the at least one mirror 20. Accordingly, the at least one aperture 50 of the pre-collimator 44 is configured and/or arranged such that primary X-ray radiation 24 and/or secondary X-ray radiation 26 can be provided to the object-receiving space 16.

Figure 5:
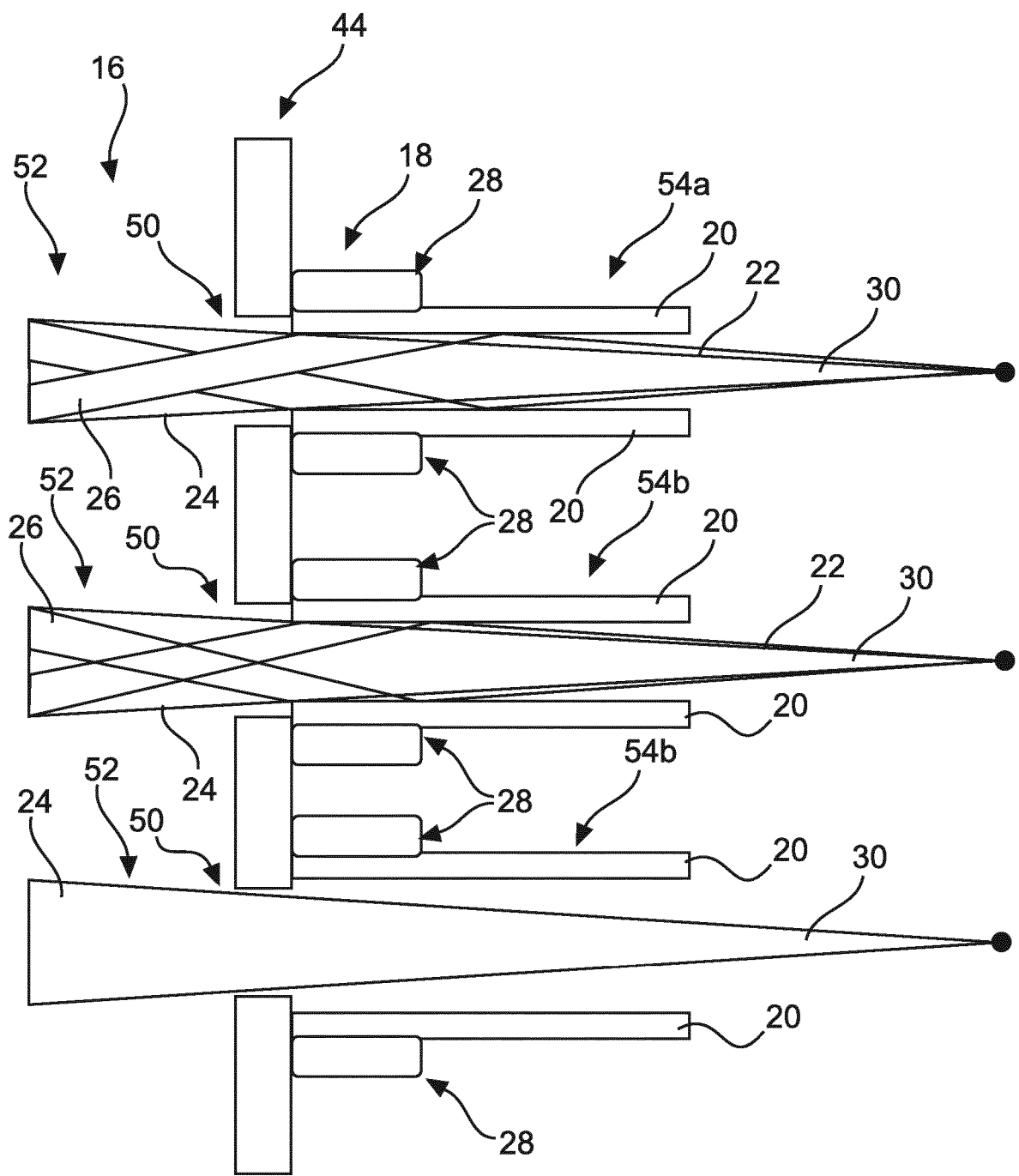
FIG. 5 shows a schematic setup of an example of the pre-collimator arrangement and the modulation arrangement.

FIG. 5 shows a further example of the pre-collimator 44 and a further example of the modulation arrangement 18.

In an example, the pre-collimator 44 comprises a plurality of pre-collimator apertures 50 for providing a plurality of X-ray beams 52 to the object-receiving space 16. The pre-collimator 44 is arranged between the modulation arrangement 18 and the object-receiving space 16. The modulation arrangement 18 comprises for each pre-collimator aperture 50 at least one associated mirror 20 of the at least one mirror 20.

As a result, the X-ray beams 52 are formed by primary X-ray radiation 24 and the secondary X-ray radiation 26. Accordingly, the X-ray beams 52 can form the X-ray radiation at the object-receiving space 16. In FIG. 5 the primary part 30 of the X-ray radiation is provided by the same source 12.

In an example, the associated mirror 20 can be replaced with an associated group 54a, 54b, 54c of two mirrors 20 for deflecting the secondary part 22 of the X-ray radiation provided by the source 12 to the associated pre-collimator aperture 50 in order to form the secondary X-ray radiation 26 in form of the X-ray beams 52.

In an example, the mirrors 20 of a first group 54a are in its first position P1. Accordingly, total reflection of the secondary part 22 of the X-ray radiation of the source 12 occurs.

In a further example, the mirrors 20 of a second group 54b are in a position between its possible first position P1 and its possible second position P2. Accordingly, total reflection of the secondary part 22 of the X-ray radiation of the source 12 occurs partly.

In a further example, the mirrors 20 of a third group 54c are in its second position P2. Accordingly, total reflection of the secondary part 22 of the X-ray radiation of the source 12 does not occur. In this case, the X-ray radiation beam 52 provided to the object receiving space 16 is formed by the primary X-ray radiation 24 only.

In an example, for each aperture 50 of the pre-collimator 44 a group 54a, 54b, 54c of at least two mirrors 20 of the mirror arrangement 18 and an actuator 28 are provided.

As a result, the intensity of the X-ray beams 52 can be controlled individually. According to a further example, a plurality of actuators 28 is provided. Preferably, each mirror 20 of the modulation arrangement 18 is coupled to one of the actuators 28 of the plurality of actuators 28. Further preferably, each mirror 20 is independently displaceable by its coupled actuator 28.

As a result, each mirror 20 of the modulation arrangement 18 can be displaced individually between its first position P1 and its second position P2. Further positions for each of the mirrors 20 can be provided, where the coupled actuator 28 can displace the respective mirror 20 at. As a result, the intensity of the X-ray beams 52 can be individually controlled.

Figure 6:
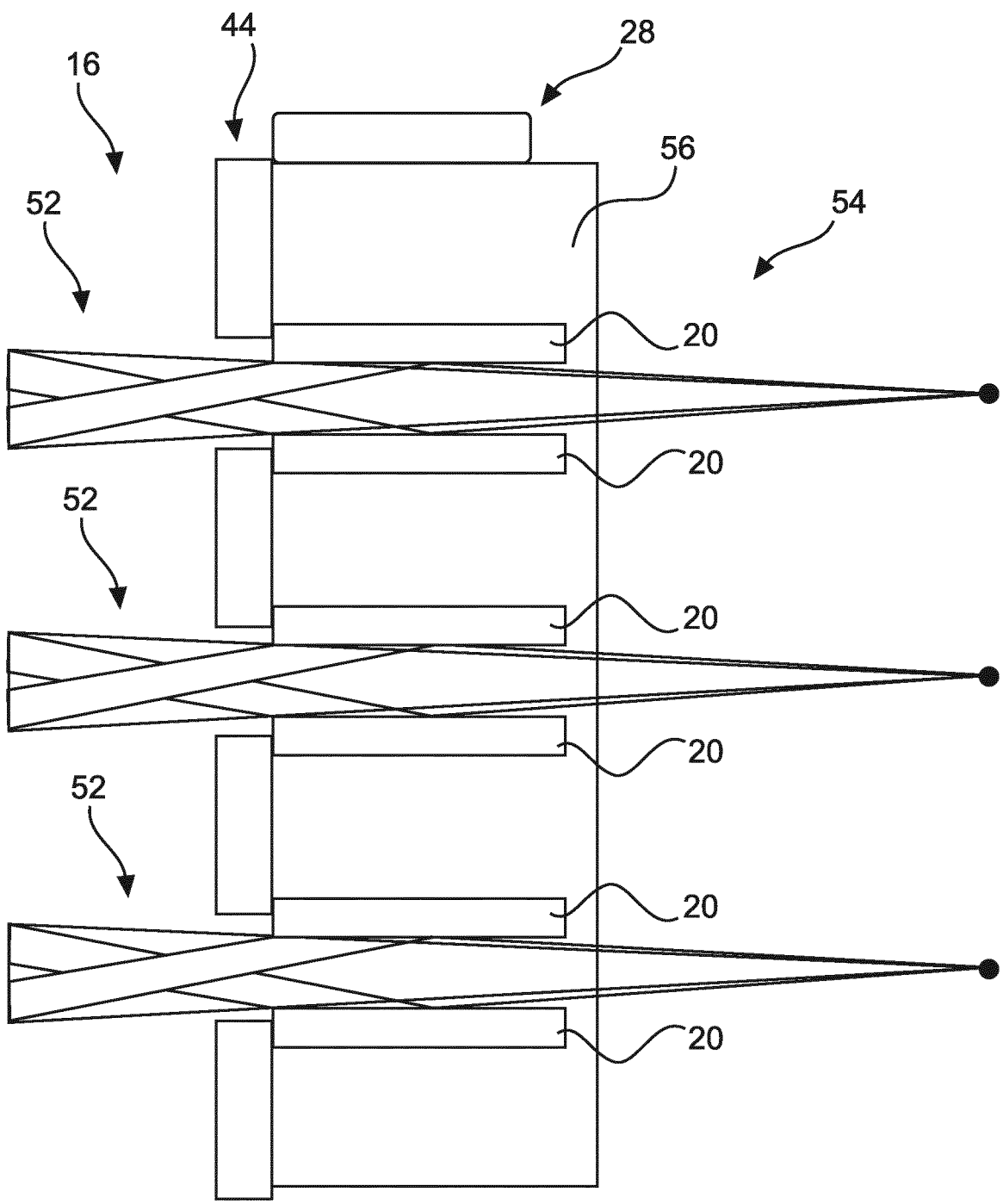
FIG. 6 shows a schematic setup of a further example of the pre-collimator arrangement and the modulation arrangement.

FIG. 6 shows a part of an exemplary embodiment of the modulation arrangement 18.

According to an example, the modulation arrangement 18 comprises a plurality of actuators 28.

In an example, a coupling element 56 is provided, which is configured to couple the actuator 28 with the group 54 of the at least two mirrors 20.

As a result, only one actuator 28 is needed for displacing the group 54 of at least two mirrors 20. Accordingly, the mirrors 20 of the group 54 are commonly displaced and thus having a similar influence on the reflection of the secondary part 22 of the X-ray radiation provided by the source 12.

As a further result, one or several X-ray beams 52 provided by the pre-collimator 44 can be controlled commonly in its intensity. Thus, a modulation of one or several beams 52 can be performed with the same actuator 28. In a further example, the modulation arrangement 18 comprises at least two actuators 28, wherein each of the actuators 28 are coupled to a group of at least four or at least six mirrors 20 of the modulation arrangement 18.

As a result, the number of actuators 28 needed for controlling the displacement of a plurality of mirrors 20 can be reduced while keeping the possibility to modulate the X-ray radiation provided to the object-receiving space 16 differently for different areas of the object-receiving space 16.

In an example, instead of the two actuators 28 as previously mentioned, the modulation arrangement 18 comprises at least ten actuators 28. Thus, the X-ray radiation intensity applied to an object of interest can be locally adapted, for instance to an attenuation of the X-ray radiation provided to the object of interest and/or its local density and/or its local thickness.

Figure 7:
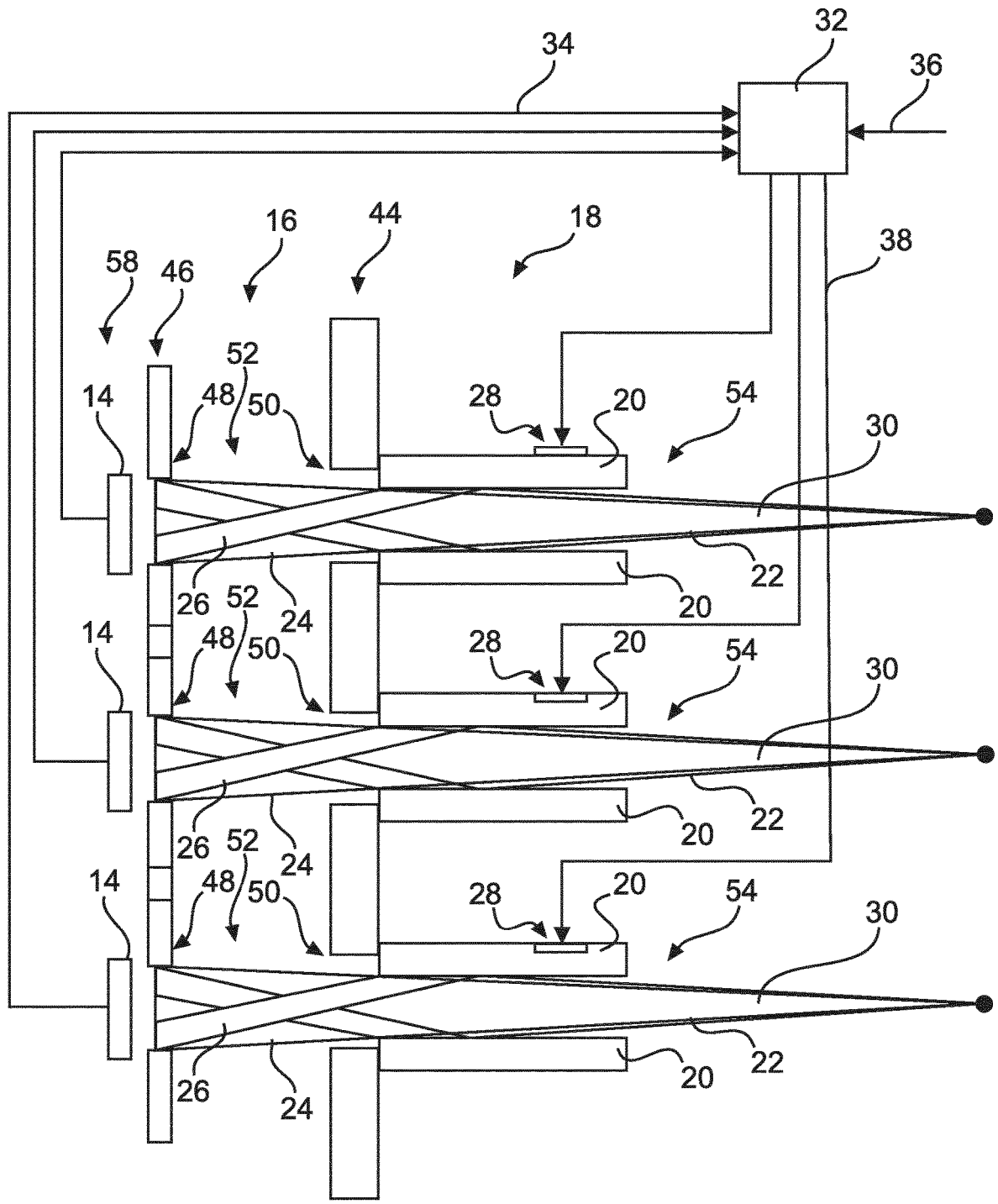
FIG. 7 shows a schematic setup of a further example of the control unit connected to the detector arrangement and the modulation arrangement.

FIG. 7 shows a schematic setup of a part of the imaging apparatus 10 comprising a control unit 32 and a detector arrangement 58.

According to a further example, the modulation arrangement 18 comprises a plurality of actuators 28. Each actuator 28 of the modulation arrangement 18 is coupled to a group 54 of at least two mirrors 20 of the modulation arrangement 18. Further, each group 54 of the mirrors 20 is commonly displaceable by the coupled actuator 28.

According to a further example, a post-collimator 46 is provided that comprises for each aperture 50 of the pre-collimator 44 an associated post-collimator aperture 48. Further, a detector arrangement 58 is provided, that comprises a plurality of detectors 14. Furthermore, the post-collimator 46 is arranged between the object-receiving space 16 and the detector arrangement 58. For each aperture 48 of the post-collimator 46, one of the detectors 14 is associated and arranged for detecting X-ray radiation passing the respective aperture 48 of the post-collimator 46, such that an aperture-dependent detector signal is provided. Further, a control unit 32 is provided to control, based on the aperture-dependent detector signal, an individual displacement of the mirrors 20 or a displacement in groups 54a, 54b, 54c of at least two mirrors 20.

In an example, for each aperture 50 of the pre-collimator 44, an associated group 54a, 54b, 54c of at least two mirrors 20 is provided. The respective group 54a, 54b, 54c of the at least two mirrors 20 can be arranged in order to influence the reflection of the secondary part 22 of the X-ray radiation provided by the source 12, which is directed to the respective aperture 50 of the pre-collimator 44. Thus, by controlling the mirrors 20 in groups 54a, 54b, 54c, the intensity of the X-ray radiation provided to the object-receiving space 16 can be controlled locally in form of an intensity of each beam 52.

In a further example (not shown), a group 54a, 54b, 54c comprises more than two mirrors 20, for example four mirrors or six mirrors. Accordingly, more than one beam 52, for example two or three beams 52, can be controlled commonly. As a result, the number of actuators 28 can be reduced.

In an example, for each aperture 48 of the post-collimator 46, an associated detector 14 is provided. The signal provided by each detector 14 preferably corresponds to the X-ray radiation detected. Further preferably, the control unit 32 is connected to each detector 14 via a signal line 34. Thus, the control unit 32 can receive the signals of the detectors 14 in order to determine the attenuation of each beam 52. Depending on the configuration of the groups 54a, 54b, 54c of mirrors 20 and the associated actuators 28, the control unit 32 can evaluate the signals provided by the detectors 14 and determine a control signal for the actuators 28, such that a suitable attenuation of the X-ray radiation provided to the object-receiving space 16 is reached. In a example, a uniform attenuation at the object receiving space 16 may be aimed.

In an example, the at least one mirror 20 abutting to one of the apertures 50 of the pre-collimator 44 is controlled by the control unit 32 depending on the detector signal of the detector 14 associated with the aperture 48 of the post-collimator 46, wherein this aperture 48 of the post-collimator 46 is associated with the aforementioned aperture 50 of the pre-collimator 44.

As a result, an aperture 50 of the pre-collimator and an aperture 48 of the post-collimator 46 can form a group with at least one associated detector 14, at least one associated mirror 20 and at least one associated actuator 28. Thus, the control unit 32 can control the modulation arrangement 18 groupwise.

FIG. 8 shows an example of a slit arrangement 60.

In an example, each aperture 50 of the pre-collimator 44 is formed as a slit.

According to a further example, each aperture 48 of the post-collimator 46 is formed as a slit.

According to a further example, the pre-collimator 44 is formed as a pre-collimator slit arrangement.

According to a further example, the post-collimator 46 is formed as a post-collimator slit arrangement.

The term "slit arrangement" can refer to pre-collimator slit arrangement and/or the post-collimator slit arrangement.

The slit arrangement 60 comprises a plurality of slits 62. A subgroup of the plurality of slits 62 are arranged parallel to an extension direction of the slits 62. A further subgroups of the slits 62 are arranged in the extension direction of the slits 62 one after another with a separating space between adjacent slits 62.

According to a further example, an X-ray imaging system (not shown) is provided. The X-ray imaging system comprises an imaging apparatus 10 according to one of the preceding examples described. The X-ray imaging system further comprises an imaging processing unit and an image data output unit. The imaging processing unit is configured to receive signals from the detector 14 or the detector arrangement 58 and to compute image data of an object based on the signals. The image data output unit is configured to provide the image data for further purpose.

In an example, the data output unit is a display for showing the image data. FIG. 9 shows a method 64 for modulating of X-ray radiation. The method 64 comprises the following:

In a first generating step 66, also referred to as step a), X-ray radiation is generated and a primary part 30 of the X-ray radiation is unreflected directed as primary X-ray radiation 24 towards a detector 14.

In a second reflecting step 68, also referred to as step b), a secondary part 22 of the X-ray radiation is reflected with a mirror 20.

In step b), the reflecting is provided as total reflection of the secondary part 22 of the X-ray radiation in order to deflect the secondary part 22 of the X-ray radiation as secondary X-ray radiation 26 towards the detector 14.

For a modulation of the X-ray radiation, step b) comprises a displacing of the mirror 20 at least between a first position P1 and a second position P2.

A ratio of an intensity of the secondary X-ray radiation 26 to an intensity of the primary X-ray radiation 24 is higher at the first position P1 of the mirror 20 than in the second position P2 of the mirror 20.

As a result, the part 22 of X-ray radiation provided towards the detector 14 can be controlled by a displacement of the at least one mirror 20. Thus, the part 22 of the X-ray radiation directed towards the detector 14 can be modulated.

According to an example, the modulated X-ray radiation is detected.

According to a further example, exemplarily shown in FIG. 10, the method 64 further comprises the following:

In a third determining step 70, also referred to as step c), an attenuation of the intensity of the X-ray radiation in form of the combination of the primary X-ray radiation 24 and the secondary X-ray radiation 26 at the object-receiving space 16 is determined.

In a fourth controlling step 72, also referred as to step d), the modulation is controlled depending on the attenuation.

According to an example, a plurality of modulator-detector-pairs is provided, each comprising a mirror 20 for reflecting the X-ray radiation in step b) and an associated detector 14. For the modulation, each mirror 20 is controlled individually depending on the attenuation of the intensity of the primary X-ray radiation 24 and/or the secondary X-ray radiation 26 at the object-receiving space 16 determined with the associated detector 14.

It has to be noted that embodiments of the invention are described with reference to different subject matters. In particular, some embodiments are described with reference to an apparatus whereas other embodiments are described with reference to the method. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single mirror or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging apparatus, comprising:
a source for generating X-ray radiation;
a detector for detecting the X-ray radiation;
an object receiving space, located between the source and the detector, for arranging an object of interest for X-ray imaging; and
an X-ray radiation modulation arrangement located between the source and the object receiving space and comprising at least one mirror configured to modulate the X-ray radiation by totally reflecting and deflecting a part of the X-ray radiation of the source towards the detector, such that a combined X-ray radiation is provided as a combination of unreflected primary X-ray radiation and reflected secondary X-ray radiation in the object receiving space;
wherein the X-ray radiation modulation arrangement further comprises at least one actuator to linearly displace the mirror between a first position and a second position, wherein the first position and the second position are along a first axis which is substantially perpendicular to a second axis between the source and the detector;
wherein a ratio of intensity of the secondary X-ray radiation to the primary X-ray radiation is higher at the first position than at the second position,
wherein the X-ray imaging apparatus further comprises a controller configured to:
determine an attenuation, in the object receiving space, of the intensity of the combined X-ray radiation as the combination of the unreflected primary X-ray radiation and of the reflected secondary X-ray radiation; and
control the X-ray modulation arrangement depending on the determined attenuation.

2. The apparatus according to claim 1, wherein the X-ray radiation generated by the source comprises at least a primary part and a secondary part, wherein the primary part has a propagation direction directly towards the detector for forming the primary X-ray radiation, wherein the secondary part has a propagation direction towards the at least one mirror in the first position; wherein the at least one mirror is arranged at least in the first position for totally reflecting radiation of the secondary part towards the detector for forming the secondary X-ray radiation.

3. The apparatus according to claim 2, wherein the at least one mirror is arranged laterally to the primary part of the X-ray radiation provided by the source.

4. The apparatus according to claim 1, further comprising a collimation arrangement, the collimation arrangement comprises a post-collimator arranged between the object receiving space and the detector.

5. The apparatus according to claim 1, wherein the X-ray radiation modulation arrangement comprises a plurality of the actuators; wherein each mirror of the X-ray radiation modulation arrangement is coupled to a corresponding actuator of the plurality of actuators; and wherein each mirror is independently displaceable by the coupled actuator.

6. The apparatus according to claim 1, wherein the X-ray radiation modulation arrangement comprises a plurality of the actuators; wherein each actuator of the X-ray radiation modulation arrangement is coupled to a group of at least two mirrors of the X-ray radiation modulation arrangement; and wherein each group of the mirrors is displaceable by the coupled actuator.

7. The apparatus according to claim 6, further comprising a post-collimator that comprises a corresponding post-collimator aperture for each aperture of a pre-collimator, further comprising a plurality of detectors, wherein the post-collimator is arranged between the object receiving space and the detector arrangement, wherein for each aperture of the post-collimator one of the detectors is associated and arranged for detecting the X-ray radiation passing the respective aperture of the post-collimator, such that an aperture-dependent detector signal is provided; and wherein a controller is configured to control, based on the aperture-dependent detector signal, an individual displacement of the mirrors or a displacement in groups of at least two mirrors.

8. The apparatus according to claim 7, wherein the pre-collimator is formed as a collimator slit arrangement.

9. An X-ray imaging system, comprising:
   an X-ray imaging apparatus according to claim 1; and
   an image processor configured to receive signals from the detector and compute image data of the object of interest based on the signals.

10. The apparatus according to claim 1, further comprising a collimation arrangement between the source and the detector, wherein the collimation arrangement comprises a pre-collimator that includes a plurality of pre-collimator apertures for providing a plurality of X-ray beams to the object receiving space, wherein the pre-collimator is arranged between the modulation arrangement and the object receiving space, and wherein the X-ray modulation arrangement comprises at least one associated mirror for each pre-collimator aperture.

11. A method for modulating X-ray radiation in an X-ray imaging device comprising a source and a detector, the method comprising:
   generating X-ray radiation;
   detecting the X-ray radiation;
   arranging an object of interest for X-ray imaging in an object receiving space located between the source and the detector;
   providing at least one mirror located between the source and the object receiving space, wherein the mirror is configured to modulate the X-ray radiation by totally reflecting and deflecting a part of the X-ray radiation of the source towards the detector, such that a combined X-ray radiation is provided as a combination of unreflected primary X-ray radiation and reflected secondary X-ray radiation in the object receiving space;
   providing at least one actuator to linearly displace the mirror between a first position and a second position, wherein the first position and the second position are along a first axis which is substantially perpendicular to a second axis between the source and the detector, and wherein a ratio of intensity of the secondary X-ray radiation to the primary X-ray radiation is higher at the first position than at the second position;
   detecting the combined X-ray radiation;
   determining an attenuation, in the object receiving space, of the intensity of the combined X-ray radiation as the combination of the unreflected primary X-ray radiation and of the reflected secondary X-ray radiation; and
   controlling modulation based on the determined attenuation.

* * * * *